(12) United States Patent
Horan

(10) Patent No.: US 6,193,514 B1
(45) Date of Patent: Feb. 27, 2001

(54) ADJUSTABLE DENTAL INSTRUMENT

(76) Inventor: Terrence L. Horan, 75 Vermont, Rte. 15, Jericho, VT (US) 05465

( * ) Notice: Subject to any disclaimer, the term of this patent is extended or adjusted under 35 U.S.C. 154(b) by 0 days.

(21) Appl. No.: 09/277,896

(22) Filed: Mar. 29, 1999

(51) Int. Cl.⁷ .................................................. A61C 3/00
(52) U.S. Cl. ........................ 433/141; 433/159; 433/163; 606/205
(58) Field of Search .................... 433/3, 4, 141, 433/146, 153, 157, 159, 163; 606/205, 208

(56) References Cited

U.S. PATENT DOCUMENTS

| | | |
|---|---|---|
| 290,103 | 12/1883 | Paul . |
| 636,285 | 11/1899 | Pinson . |
| 649,234 | 5/1900 | Chiavaro . |
| 673,541 * | 5/1901 | Hussey . |
| 770,162 * | 9/1904 | Chase ..................................... 433/159 |
| 778,977 | 1/1905 | Johnson . |
| 1,202,698 * | 10/1916 | Ford . |
| 1,412,130 | 4/1922 | Onderdonk . |
| 2,776,152 | 1/1957 | Ianuzzi . |
| 3,368,553 | 2/1968 | Kirby . |
| 3,748,741 * | 7/1973 | Yerkes, Jr. ........................... 433/167 |
| 3,898,738 * | 8/1975 | Linder ................................... 433/159 |
| 4,364,730 * | 12/1982 | Axelsson ............................... 433/141 |
| 4,620,813 | 11/1986 | Lacher ................................... 403/93 |
| 4,759,713 | 7/1988 | Heiss et al. ........................... 433/141 |
| 4,976,617 | 12/1990 | Carchidi ............................... 433/141 |
| 4,997,382 * | 3/1991 | Berger .................................. 433/163 |
| 5,851,211 * | 12/1998 | Khoury ................................ 606/208 |
| 5,928,263 * | 7/1999 | Hoogeboom ........................ 606/205 |

OTHER PUBLICATIONS

Product Information Sheet entitled Detsch® Scalpel Handles–Blade Breaker–Scalpel Blades, G. Hartzell & Son, date: at least as early as Jan. 19, 1998.
Clinician's Choice Dental Products Inc. (p. 21 from catalog) (no date).

* cited by examiner

Primary Examiner—Ralph A. Lewis
(74) Attorney, Agent, or Firm—Downs Rachlin & Martin PLLC

(57) ABSTRACT

A dental instrument (10) having a tool (100) with a tip (108) capable of being rapidly adjusted and fixed in a variety of orientations relative to an instrument body (14). The instrument comprises opposing jaws (22 and 32) having concave surfaces (26 and 36). One jaw (22) is attached to one end of the instrument body, while the other jaw (32) is attached to the end of a lever arm (40). The lever arm is pivotally attached to the instrument body and is pivotal between a first (closed) position (P1), a second (intermediate) position (P2) and a third (open) position (P3). The lever arm includes a latch (50) which releasably grips the instrument body so as to retain the lever arm in the first (closed) position. The tool includes a spherical ball-end sized to be tightly engaged by the concave surfaces of the jaws when the lever arm is in the first (closed) position, thereby preventing the tool from moving relative to the instrument body.

25 Claims, 10 Drawing Sheets

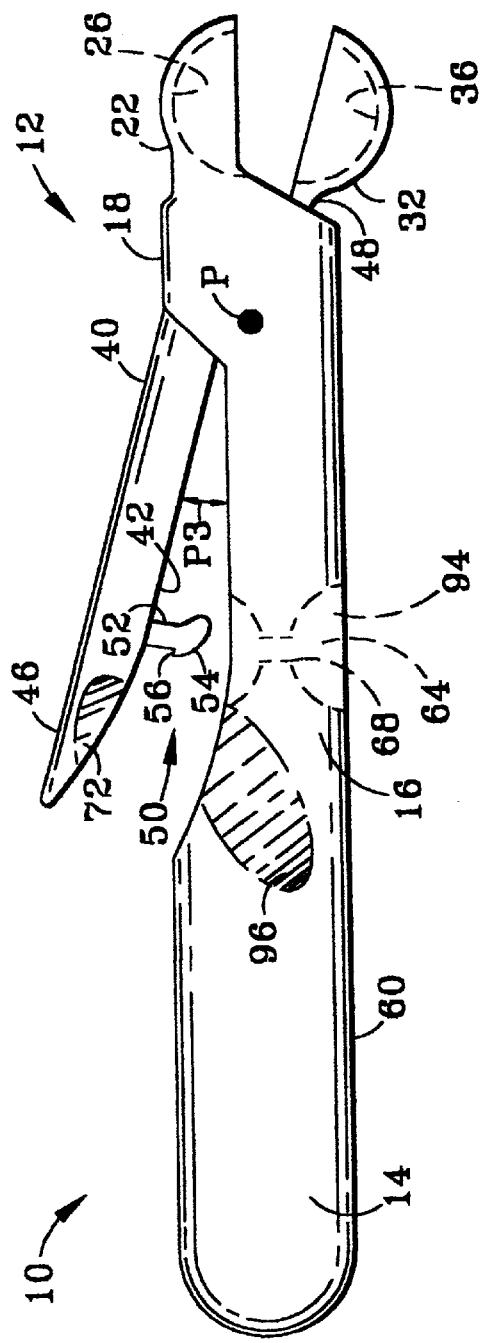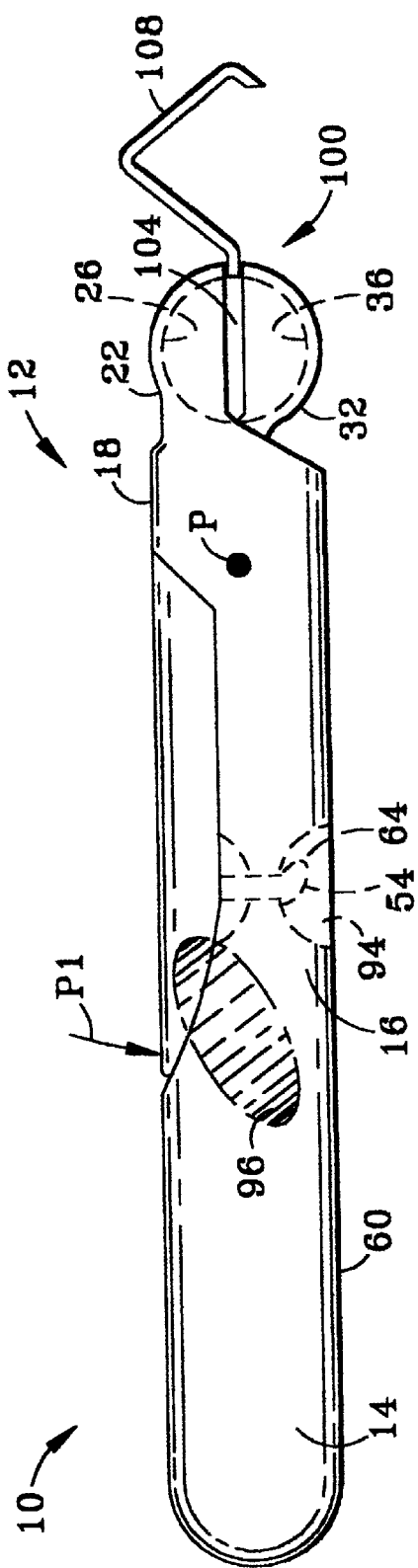
FIG. 1
FIG. 2

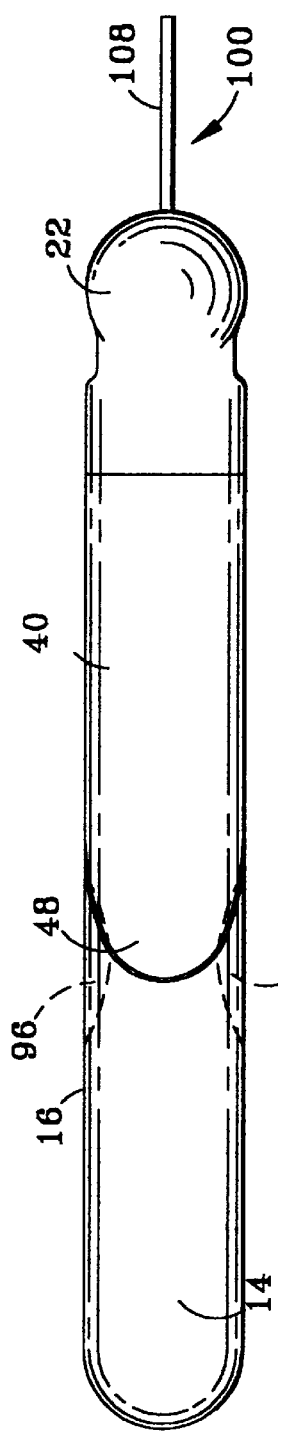
FIG. 5
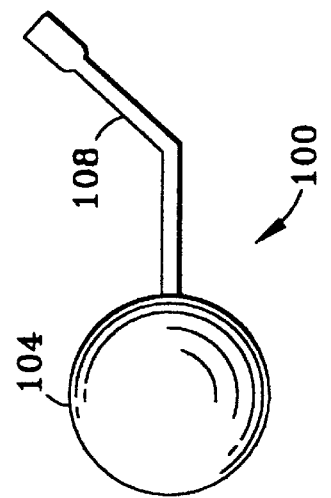
FIG. 6c
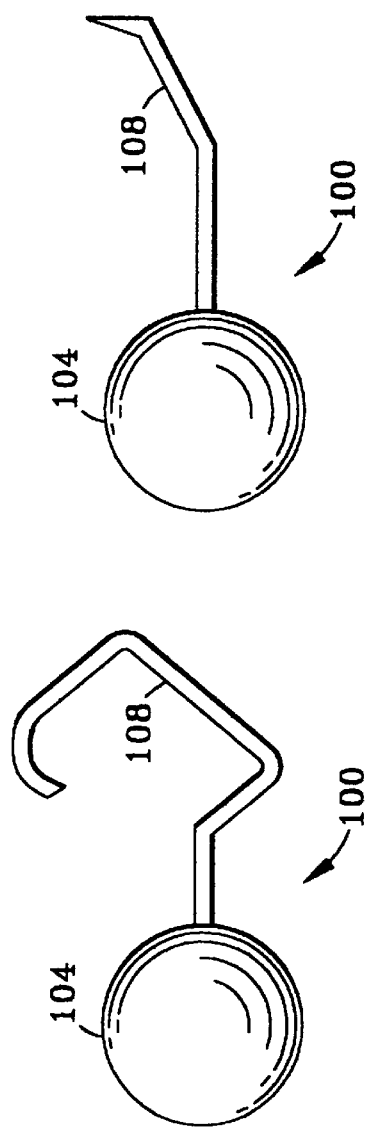
FIG. 6b
FIG. 6a

ADJUSTABLE DENTAL INSTRUMENT

FIELD OF THE INVENTION

The present invention relates to mechanical instruments, and in particular to dental instruments which can hold a tool tightly in a variety of positions and which allows for the tool to be quickly and easily moved from one position to another.

BACKGROUND OF THE INVENTION

In the practice of dentistry, it is often necessary for a dentist to perform dental procedures at various orientations relative to the dental work. This typically requires the dentist to have a variety of dental instruments at their disposal, each having at one or both ends a fixed tool with a tip having a given shape and orientation. Alternatively, the dentist can use a dental instrument comprising an instrument body that accepts a tool having a tip. The tool can be adjusted so the tip can take on a variety of orientations (i.e., positions) relative to the instrument body. In addition, with some instruments, the tool may be replaced with another tool having a different tip configuration. For such adjustable dental instruments, it is important that the tool be capable of being rapidly adjusted to a particular orientation and then fixed tightly in place within the instrument body. It is also important that the instrument body and tool be amenable to being rapidly cleaned for subsequent re-use.

As an example of such an instrument, U.S. Pat. No. 649,234 discloses a dental tool with a tool having a ball-end disposed in a concave socket screwed into one end of the instrument. The socket has an aperture with recesses through which the instrument tip extends. The ball-end is held in place within the concave socket by tightening a threaded rod running along the axis of the instrument handle which pushes the ball-end into the socket. While the orientation of the instrument tip of the tool is adjustable, the locking mechanism is such that adjustment cannot be accomplished rapidly. Moreover, the configuration of the aperture through which the instrument tip protrudes limits the number of orientations available.

U.S. Pat. No. 1,412,130 discloses a dental "scaler" comprising two hemispherical sections, each having a tapered end which is inserted into a hollow tube serving as the instrument body. The tapered ends are connected to a threaded rod running the length of the tube. The ball-end of a tool is inserted within the hemispherical sections. When the threaded rod is tightened, the tapered ends of the hemispherical sections are drawn into the tube, thereby causing the hemispherical sections to firmly grasp the ball-end placed therein. While this dental instrument also allows the orientation of the instrument tip of the tool to be adjusted, the locking mechanism is such that the adjustment is time consuming. Also, the clamping force on the ball-end is proportional to the degree to which the threaded rod is tightened. This is not desirable, since this procedure introduces uncertainty as to the strength in which the instrument tip is being held.

A dental instrument presently on the market and based on the concept of locking the tool by a screw-type mechanism is the "Zekyra," sold by Clinician's Choice™ Dental Products, Inc., of New Milford, Conn. The instrument comes with "protector tips" (i.e., tools) which are adjustable and locked into place relative to an instrument body, using a screw-type (i.e., threaded) locking mechanism.

In addition to dental devices, there are prior art patents which disclose devices for holding a tool having a ball-end. For example, U.S. Pat. No. 778,977 discloses a coupling device (a "Pitman coupling") comprising two arms each having hemispherical sections at their respective ends, wherein one of the arms is fixed to a body portion, while the other arm pivots about a pivot pin relative to the body portion. The pivotable arm is wedge-shaped at the end opposite the hemispherical section. A spring-loaded take-up wedge fits snugly against and pushes on the wedge-shaped end of the pivotable arm, thereby causing the hemispherical sections to grasp a ball-end placed therein. Unfortunately, this design also is such that the adjustment of the instrument tip attached to the ball-end cannot be achieved rapidly. Also, the coupling disclosed is not particularly well-suited for a dental instrument, since it is mechanically complex and appears to be incapable of readily providing enough force to hold the ball-end sufficiently tightly for dental applications.

U.S. Pat. No. 4,620,813 discloses a position-retaining mechanism having two hemispherical sections at the end of respective arms, each having a regular pattern of protrusions on their inner surfaces, and a ball-end having complimentary recesses, wherein the ball-end fits between the two hemispherical sections. The arms are pivotable about a pivot point and the ball-end is held snugly between the hemispherical sections by a spring which forces the arms apart, thereby forcing the hemispherical sections together. However, this position retaining mechanism is not particularly well-suited for a dental instrument, since the spring-type locking device would likely not provide sufficient clamping strength to hold the ball-end fixed while performing dental procedures. In addition, the number of orientations of an instrument tip attached to the ball-end would be limited. Moreover, the mechanism appears rather complicated to fabricate.

SUMMARY OF THE INVENTION

The present invention relates to mechanical instruments, and in particular to dental instruments which can hold a tool tightly in a variety of positions and which allows for the tool to be quickly and easily moved from one position to another.

A first aspect of the present invention is an instrument comprising an instrument body having a first end. A first jaw is attached to the first end, the first jaw having a first concave surface. Also included is a second jaw having a second concave surface, and a lever arm. The lever arm has first and second ends, with the first end being attached to the second jaw. The lever arm is pivotally attached to the instrument body adjacent the first end so as to be pivotable from a first position. The instrument further includes a latch attached to either the lever arm or the instrument body. The latch releasably grips the other of the lever arm and instrument body so as to retain the lever arm in the first (closed) position. The instrument also includes a tool having a spherical ball-end that is sized to be tightly engaged by the first and second concave jaw surfaces when the lever arm is in the first position so as to prevent the tool from moving relative to the instrument body. The ball-end may be incompressible or compressible.

A second aspect of the invention is an instrument as described above, wherein the instrument body includes a surface having an aperture with a rim surrounding the aperture. The aperture is located so as to receive the latch. The latch includes a bulbous end having a lip, and the end is sized to fit through the aperture such that the lip is capable of engaging the rim when the lever arm is in the first position. This mechanism allows the lever arm to be snap-latched and snap-released, thereby providing for rapidly changing tools or rapidly adjusting of the orientation of the tip of the tool, while also engaging the ball-end with sufficient strength to hold the tool stationary relative to the instrument body while performing dental work.

A third aspect of the invention is an instrument wherein each end of the instrument body includes the dental instrument as described above.

BRIEF DESCRIPTION OF THE DRAWINGS

FIG. 1 is a side elevation view of one embodiment of the dental instrument of the present invention, showing the jaws in the open position;

FIG. 2 is a side elevation view of the dental instrument of FIG. 1, showing the jaws in the closed position holding a tool;

FIG. 5 is a top view of the dental instrument shown in FIG. 1;

FIGS. 6a–6c show three different types of tools suitable for use with the dental instrument of the present invention;

DETAILED DESCRIPTION OF THE INVENTION

Figure 3:
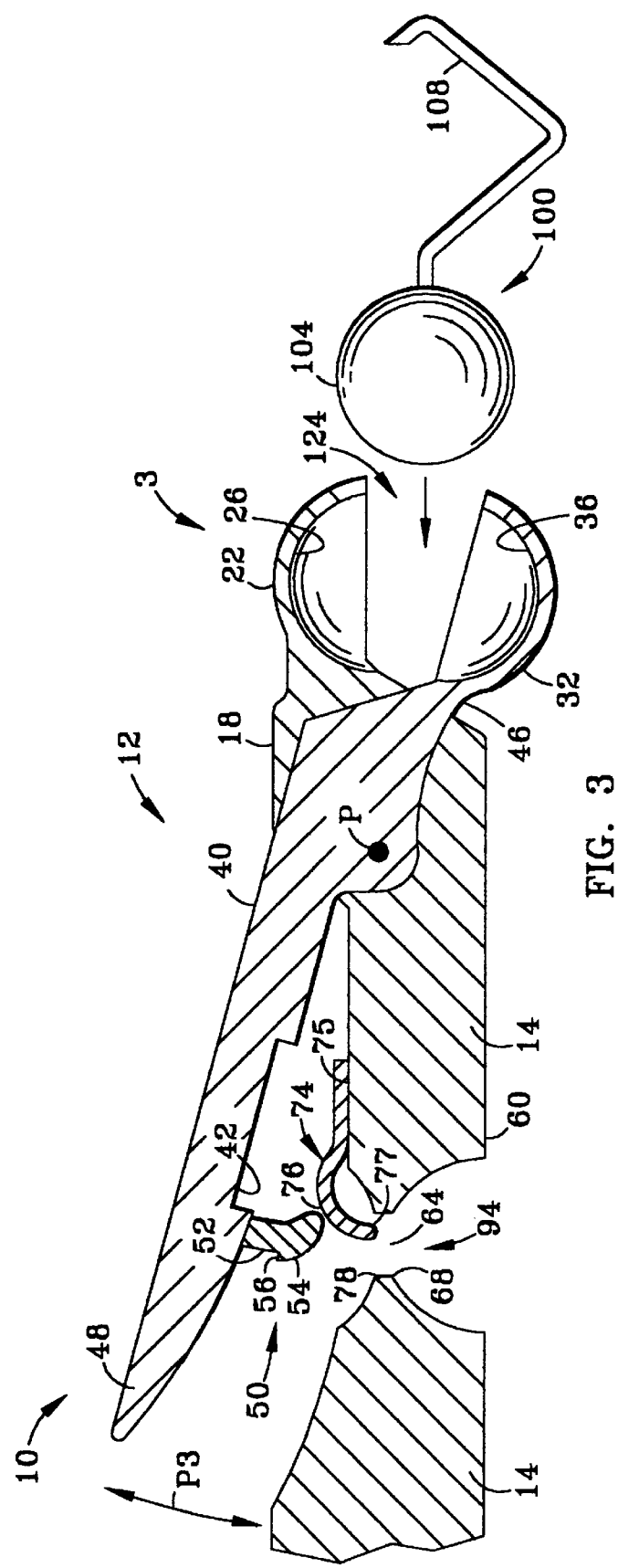
FIG. 3 is an enlarged partial cross-sectional view along the longitudinal axis of the dental instrument in FIG. 1, shown with a tool to be inserted into the instrument.

The present invention relates to mechanical instruments, and in particular to dental instruments which can hold a tool tightly in a variety of positions and which allows for the tool to be quickly and easily moved from one position to another.

With reference to FIGS. 1 and 2, the present invention is an adjustable dental instrument 10, shown in a preferred single-ended embodiment. In an alternate embodiment, instrument 10 has identical ends 12, as discussed below. Instrument 10 comprises an instrument body 14 having sides 16, and a first end 18 with a first jaw 22 attached thereto. First jaw 22 has an inner concave surface 26. Instrument 10 further includes a second jaw 32 having an inner concave surface 36, and a lever arm 40 with an underside 42, first end 46 and second end 48. Second end 48 is attached to second jaw 32. Lever arm 40 is pivotally attached at pivot point P to instrument body 14 adjacent first end 18. Lever arm 40 is pivotable between a closed position P1 (as shown in FIG. 2), an intermediate position P2, and an open position P3 (as shown in FIG. 1). An advantage of having an open position P3 is that the process of cleaning the parts of the instrument within instrument body 14 is simplified.

In an exemplary embodiment, lever arm 40 is approximately 60 mm, and pivot point P is located approximately 18 mm from lever arm end 48. Also, the total length of lever arm 40 and second jaw 32 is approximately 80 mm. This configuration provides a mechanical advantage of approximately 3 to 1, which is suitable for providing a sufficient clasping force, as described below. The present invention encompasses lever arms 40 of varying length, with the length of the lever arm being chosen to achieve the desired clamping force.

With continuing reference to FIGS. 1 and 2 and also referring to FIG. 3, instrument 10 further includes a latch 50 attached to underside 42 of lever arm 40 at or near first end 46. Latch 50 includes a flexible stem 52 with a bulbous end 54 attached thereto. End 54 has a lip 56. Instrument body 14 also includes a surface 60 having an aperture 64 with a rim 68 surrounding the aperture. Aperture 64 is located and sized so as to receive latch 50 when lever arm 40 is in closed position P1 (see FIG. 2). In an alternate embodiment, latch 50 is attached to instrument body 14, and aperture 64 with rim 68 are located in lever arm 40.

In a first embodiment of the present invention, adjacent aperture 64 is a lever spring 74, which is attached to instrument body 14 near the aperture. Lever spring 74 is designed so as to receive latch 50 with a loose friction fit, and is capable of being deformed so as to readily release latch 50, as described below. In addition, lever spring 74 may also be designed to push lever arm 40 away from instrument body 14 and into intermediate position P2 when latch 50 is released, as described below. To this end, lever spring 74 preferably engages underside 42 of lever arm 40 when the lever arm is in closed position P1. Accordingly, lever spring 74 preferably comprises a flat end portion 75 attached to body 14, and a curved (e.g., hook-shaped) flexible portion 76 having an end 77. Flexible portion 76 extends toward a radially extending inner wall 78 of instrument body 14 adjacent aperture 64, and end 77 extends downward toward the aperture.

The curvature of portion 76 is such that bulbous end 54 of latch 50 deforms lever spring 74 and thereby passes through aperture 68 when lever arm 40 travels from open position P3 or intermediate position P2 to closed position P1, but is stopped by end 77 when the lever arm travels from closed position P1 to intermediate position P2. An advantage of having lever spring 74 designed as described above rather than, for example a coiled spring, is that the former is more readily cleaned and sterilized, which is an important aspect of the present invention.

Figure 4:
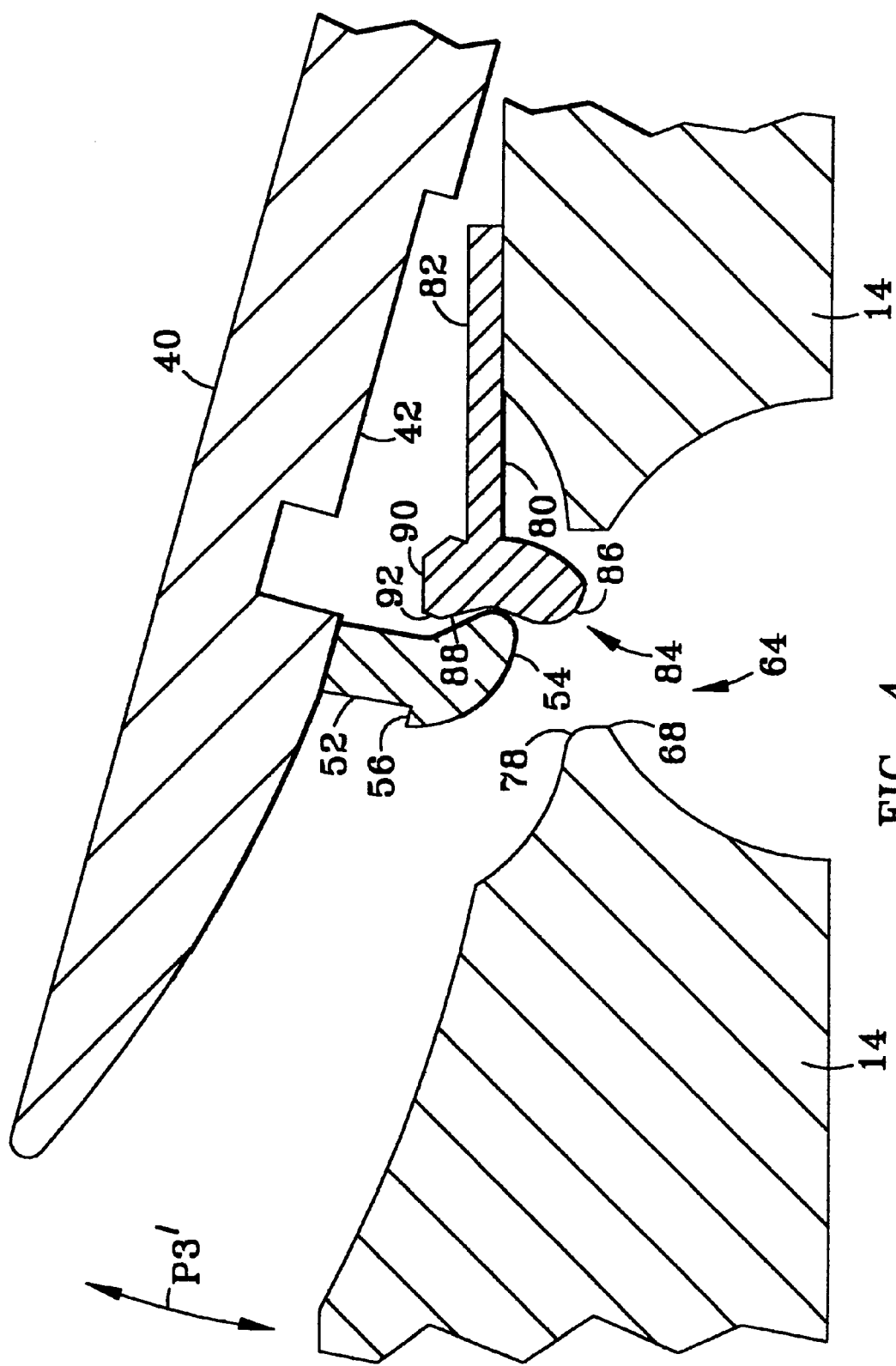
FIG. 4 is a close-up partial cross-sectional view down the longitudinal axis of the dental instrument in FIG. 1 of an alternate embodiment of the dental instrument shown in FIG. 1, with a latch-receiving member in place of the lever spring.

With reference now to FIG. 4, in a second embodiment of the present invention, lever spring 74 in apparatus 10 (FIG. 1) is replaced by a latch-receiving member 80, which is also attached to instrument body 14 near aperture 64. Member 80 is designed so as to receive latch 50 with a loose friction fit and is preferably substantially rigid, but need not be so. Member 80 includes a flat end portion 82 attached to body 14, and an end 84 extending toward inner wall 78. End 84 includes an outwardly rounded section 86, an inwardly curved section 88 and a top edge 90 adjacent the curved section. Top edge 90 preferably includes a bevel 92 nearest curved section 88. The operation of latch-receiving member is similar to that of lever spring 74 and is discussed below.

With reference to FIGS. 1 and 5, in one embodiment of the present invention, surface 60 includes a first depression 94 surrounding aperture 64 to facilitate manually adjusting instrument 10, as described in detail below. Also, in another embodiment of the present invention, at least one of instrument body sides 16 includes a second depression 96 (FIG. 5) located at or near the mid-section of instrument 10 and which overlaps with second end 48 of lever arm 40. Depression 96 is also designed to facilitate manually adjusting instrument 10, as described in detail below.

With continuing reference to FIG. 1 and also to FIGS. 6a–6c, instrument 10 further includes a tool 100 having a spherical ball-end 104 that is sized to be tightly engaged by jaw concave surfaces 26 and 36 when lever arm 40 is in first position P1. In a preferred embodiment of the present invention, concave surfaces 26 and 36 have a radius of curvature of 6 mm to 8 mm (e.g, 7 mm) and ball-end 104 has a matching radius, or one that is slightly larger. Ball-end 104 may comprise an incompressible material, such as stainless steel, or a compressible material, such as rubber or silicone. Tool 100 also includes an instrument tip 108, which can have any one of a number of configurations common in dental instruments, such as shown in FIGS. 6a–6c.

An important aspect of the present invention is that ball-end 104 is engaged with sufficient force by jaw concave surfaces 26 and 36 so that the ball end remains immobile within jaws 22 and 32 and does not move relative to instrument body 14 when conventional dental forces are applied to tip 108. A preferred way this is accomplished is by designing concave surfaces 26 and 36 and ball-end 104 to have either an interference fit or a precision fit when lever arm 40 is in first position P1. The length of lever arm 40 and the location of pivot point P at end 18 of instrument body 14 provides the leverage necessary to provide jaws 22 and 32 with sufficient force to strongly clasp ball-end 104. In additional, jaws 22 and 32 may include a compressible liner on surface 26 and 36 to facilitate snugly gripping ball-end 104.

Figure 8:
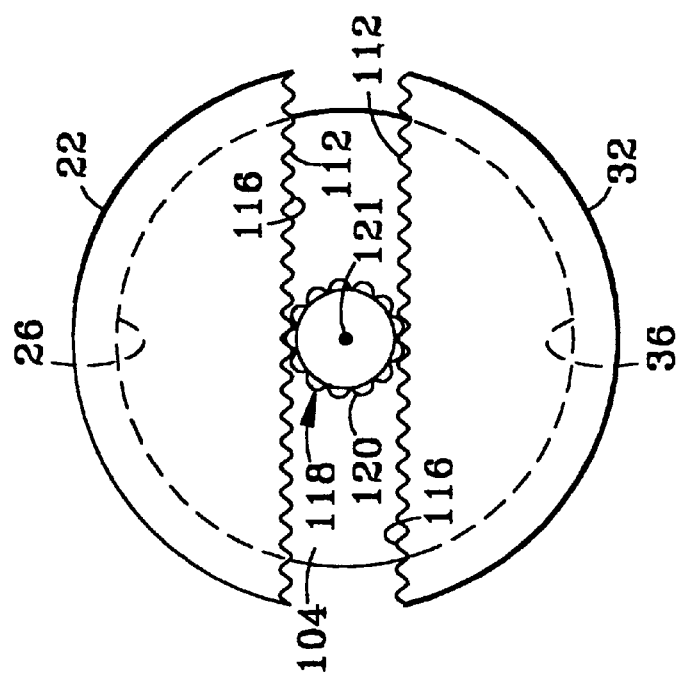
FIG. 8 is an end view of the dental instrument shown in FIG. 7.
Figure 7:
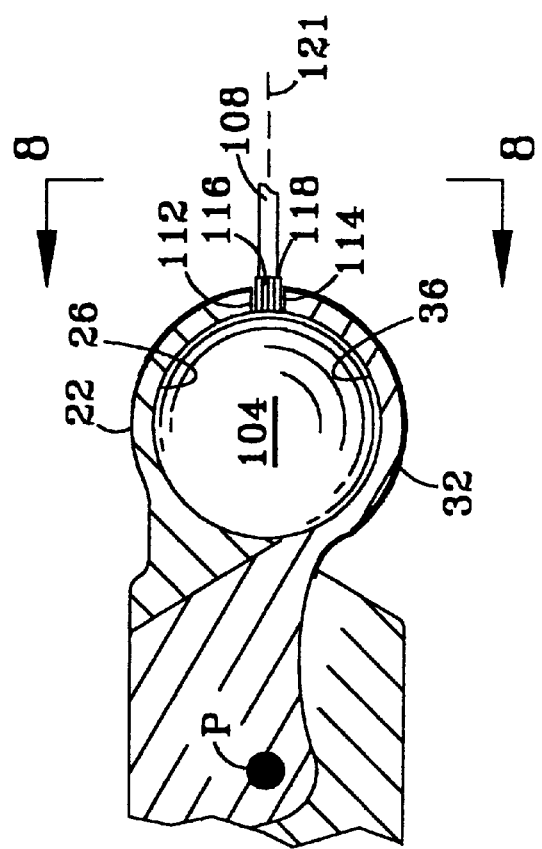
FIG. 7 is an enlarged partial cross-sectional view along the longitudinal axis of a second embodiment of the dental instrument of the present invention similar to that in FIG. 1, in which the concave jaw surfaces and the tool neck are provided with teeth.

With reference now to FIGS. 7 and 8, concave surfaces 26 and 36 have outer edges 112 and 114, respectively, that preferably include teeth 116. Further, tool 100 includes a neck 118, located between ball-end 104 and tip 108, which preferably includes teeth 120 designed so as to mesh with teeth 116 when lever arm 40 is in closed position P1, as shown in FIG. 8. This configuration adds to the ability of jaws 22 and 32 to maintain ball end 104 immobile therein and with respect to instrument body 14 when tip 108 is subject to conventional dental forces by preventing rotation of tool 100 about central axis 121 of neck 118.

Figure 13:
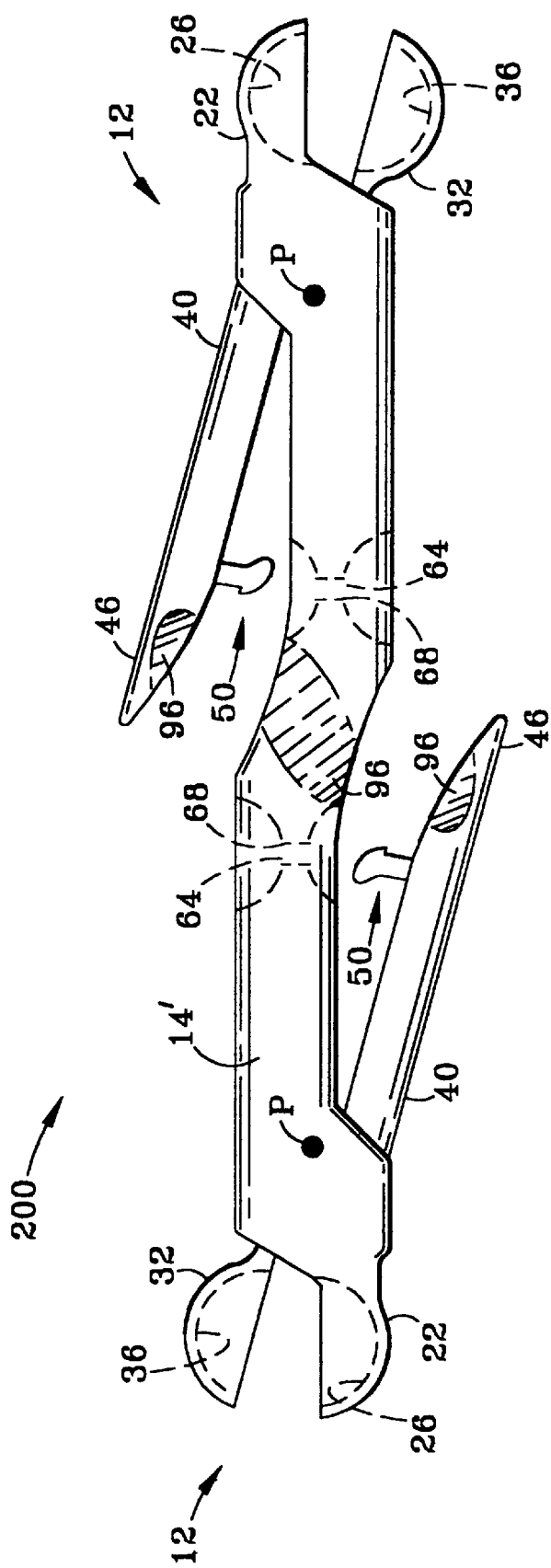
FIG. 13 is an alternate embodiment of the dental instrument present invention similar to FIG. 1, except the instrument has identical ends.

With reference to FIGS. 1 and 13, in another embodiment of the present invention, dental instrument 200 is configured to have identical ends 12, like instrument 200 in FIG. 13. Instrument 200 includes the same elements as instrument 10 of FIGS. 1 and 2, excepts that both ends 12 are included on a single instrument body 14'.

The operation of instrument 10 is now described. With reference to FIG. 3, lever arm 40 is manually adjusted so as to be in open position P3. If lever arm 40 is in closed position P1, adjusting the lever arm to be in open position P3 is accomplished by unlatching the lever arm (as discussed below), which then places the lever arm in position P2. A finger is then inserted into depression 96 and an upward force applied to the lever arm. Depression 96 provides a location on lever 40 to which such a force may be applied. Depression 96 is provided to facilitate opening lever arm 40, since without the depression the lever arm would be flush with sides 16 of instrument body 14. For this reason, depression 96 is an important, although non-essential, aspect of instrument 10. In an alternate preferred embodiment, depression 96 is provided only on outer surface 60 and does not extend to lever arm 40, so that the lever arm overhangs sides 16, thereby forming a lip to which an upward force may be applied.

An upward force applied to lever arm 40 causes jaw 22 to rotate around pivot point P and separate from jaw 32, thereby opening jaws 22 and 32 so ball-end 104 can be inserted therebetween. A particular tool 100, such as one shown in FIGS. 6a–6c, is then selected based on the dental procedure to be performed. Ball-end 104 of tool 100 then is placed between jaws 22 and 32, with tip 108 preferably having at least the general orientation desired.

Figure 9:
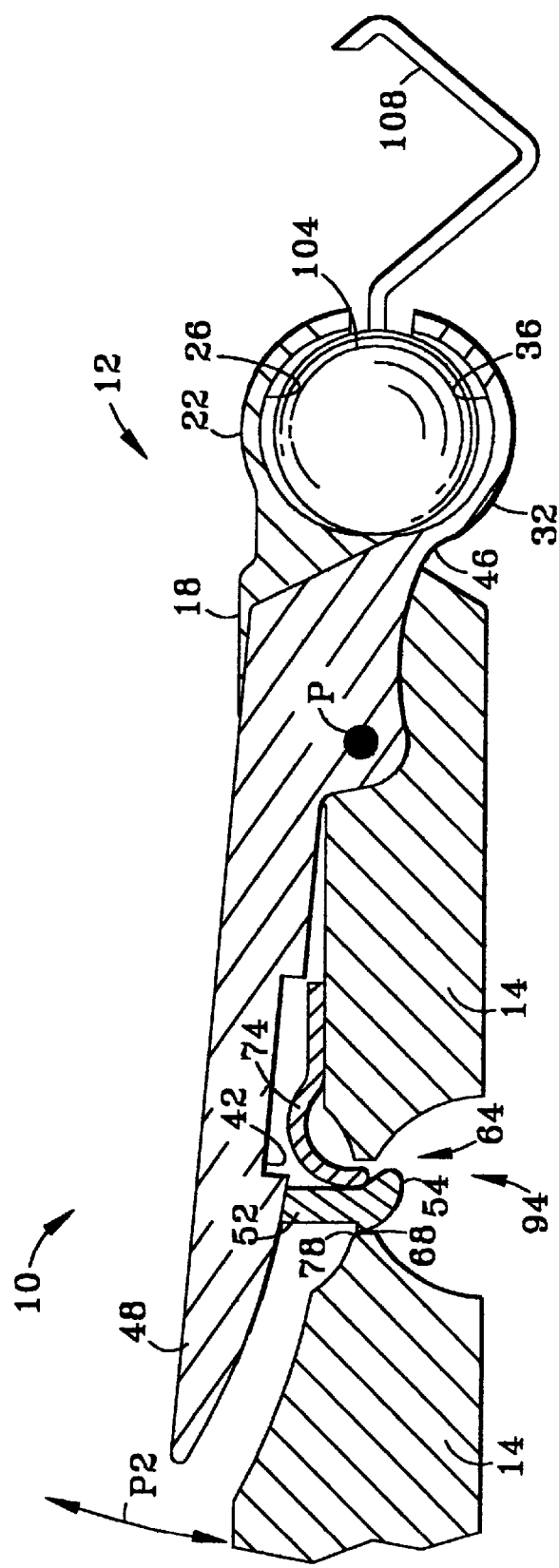
FIG. 9 is similar to FIG. 3, except the tool end is within the jaws and the lever arm is in the intermediate position.

Now, with reference to FIG. 9, lever arm 40 is then depressed toward instrument body 14, thereby bringing concave surfaces 26 and 36 closer to ball-end 104. As lever arm 40 approaches intermediate position P2, concave surfaces 26 and 36 begin to engage ball-end 104. Simultaneously therewith, latch end 54 brushes between lever spring 74 and inner wall 78. The brushing of latch end 54 against inner wall 78 causes stem 52 to flex somewhat from its original shape, as the latch moves toward aperture 64. At this point, tip 108 can be precisely adjusted to the desired orientation relative to instrument body 14.

Figure 10:
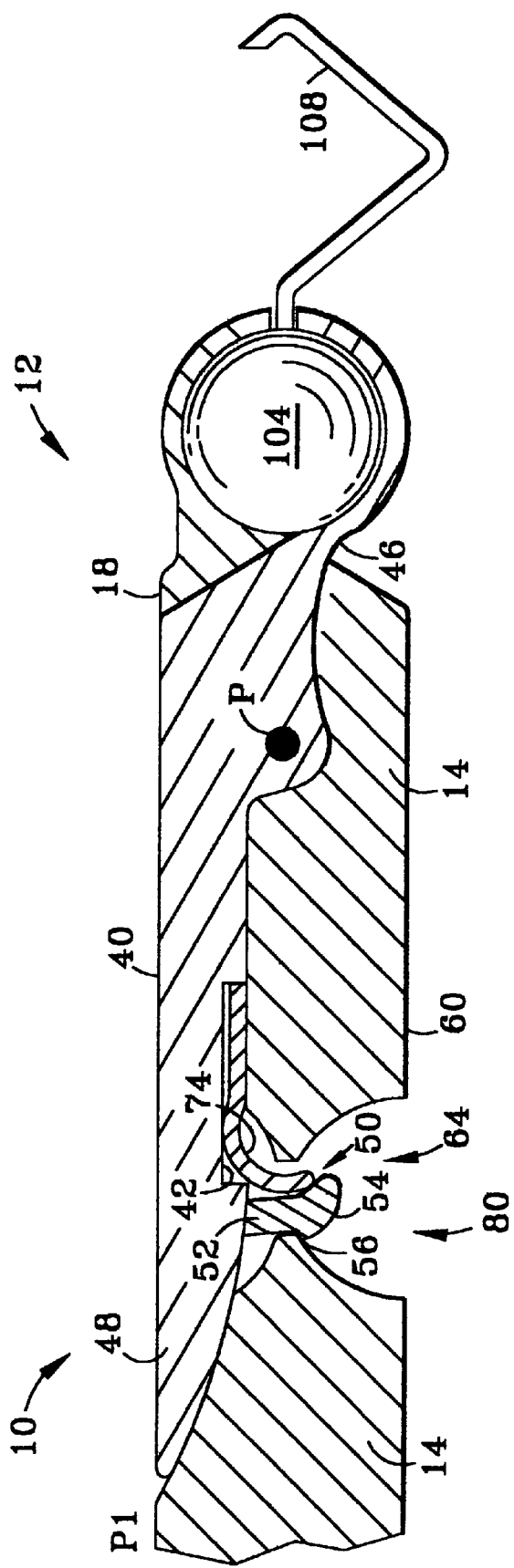
FIG. 10 is similar to FIG. 9, except the lever arm is in the closed position.

With reference now to FIG. 10, as lever arm 40 is brought flush with surface 16 and into closed (i.e., latched) position P1, latch end 54 passes through aperture 64, whereupon stem 52 flexes back into its original shape, thereby causing lip 56 to abruptly overlap (i.e., "snap-latch" with) rim 68. Simultaneously therewith, concave surfaces 26 and 36 tightly engage ball-end 104 so as to prevent tool 100 from moving relative to instrument body 14. At this point, instrument 10 is ready to be used to perform a dental procedure.

In the present invention, the flexing of stem 52 necessary to disengage lip 56 with rim 68 when in position P1 provides latch 50 with spring energy, allowing the latch to assist in pushing lever arm 40 away from instrument body 14. However, lever spring 74 may be designed to be compressed when lever arm 40 is in closed position P1. This provides additional latching force, as well as an additional force for pushing lever arm 40 away from instrument body 14 when latch 50 is released.

Tool 100 can be rapidly adjusted or the tool can be rapidly replaced with another tool using the above-described snap-latching procedure. With reference now to FIGS. 9 and 10, when the orientation of tip 108 needs to be adjusted, a person using instrument 10 places a finger into first depression 94 and exerts a force on latch end 54 toward first end 18 (FIG. 10), which causes lip 56 to abruptly disengage (i.e., "snap-release" from) rim 68 (FIG. 9). If a lever spring 74 is used, it may be designed to be compressed while lever arm in position P1, as described above. If so, spring 74 then pushes lever arm 40 away from closed position P1 toward intermediate position P2. Otherwise, the spring force stored in latch 50 upon flexing stem 52 to disengage lip 56 of latch end 54 with rim 68 serves to push lever arm 40 away from instrument body 14, as described above.

Depression 94 facilitates the snap-release of latch end 54 by providing a surface contoured to a person's finger. Depression 94 also optionally permits latch 50 to be sized so that end 54 does not extend beyond lower surface 60, thereby preventing accidental release of the latch. Once lip 56 snap-releases from rim 68, lever arm 40 moves away from instrument body 14, thereby lifting latch end 54 through aperture 64, while simultaneously causing concave surfaces 26 and 36 to loosen their grip on ball-end 104.

With continuing reference to FIGS. 9 and 10, at this point latch end 54 becomes pinned between lever spring 74 and inner wall 78 so that lever arm 40 opens only to intermediate position P2. In this position, ball-end 104 is held sufficiently loosely within concave surfaces 26 and 36 so that the orientation of tip 108 can be precisely adjusted, if necessary. At the same time, concave surfaces 26 and 36 are held sufficiently close to one another that ball-end 104 does not fall out of jaws 22 and 32. After tip 108 is adjusted to have a desired orientation, lever arm 40 is again depressed and snap-latched into closed position P1, thereby driving jaws 22 and 32 together so that ball-end 104 is tightly engaged by concave surfaces 26 and 36, as described above.

Figure 11:
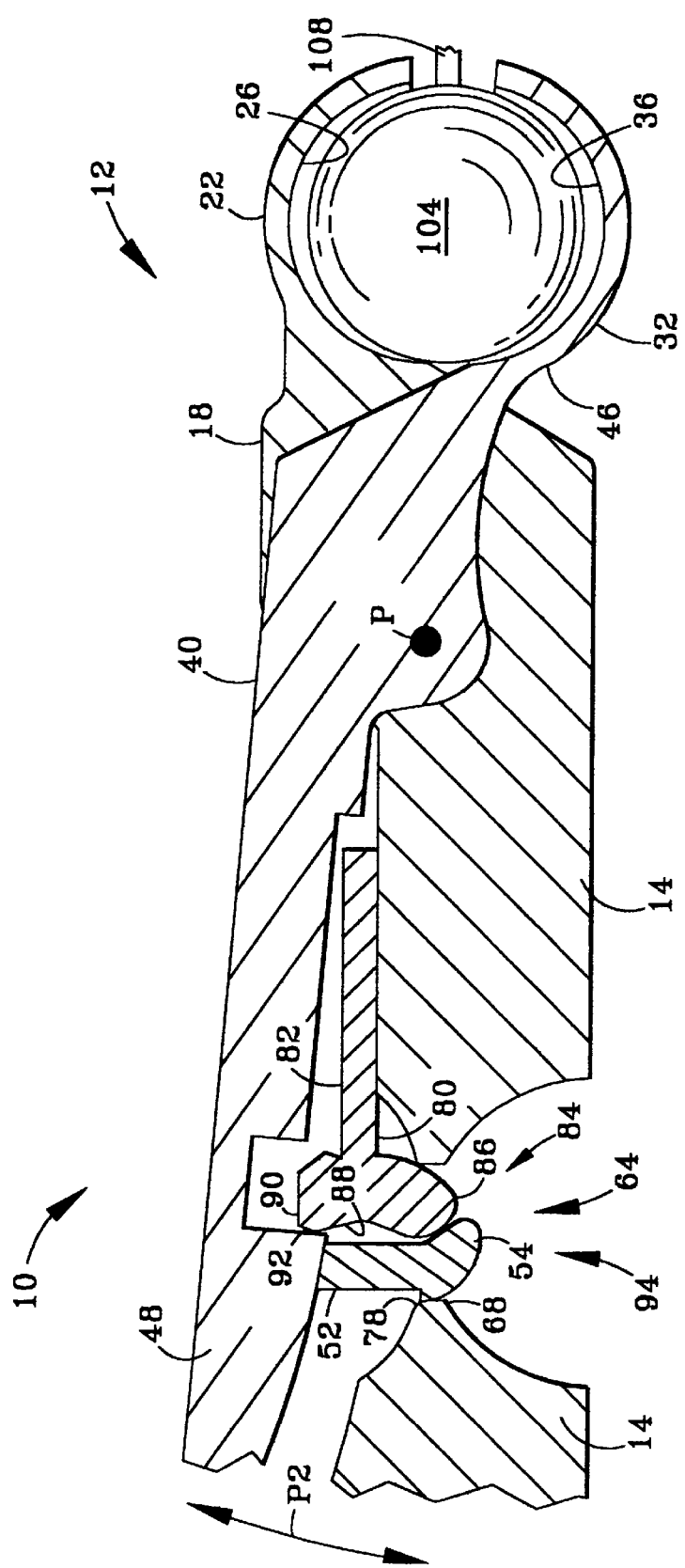
FIG. 11 is similar to FIG. 9, except that the lever spring is replaced with a latch-receiving member.
Figure 12:
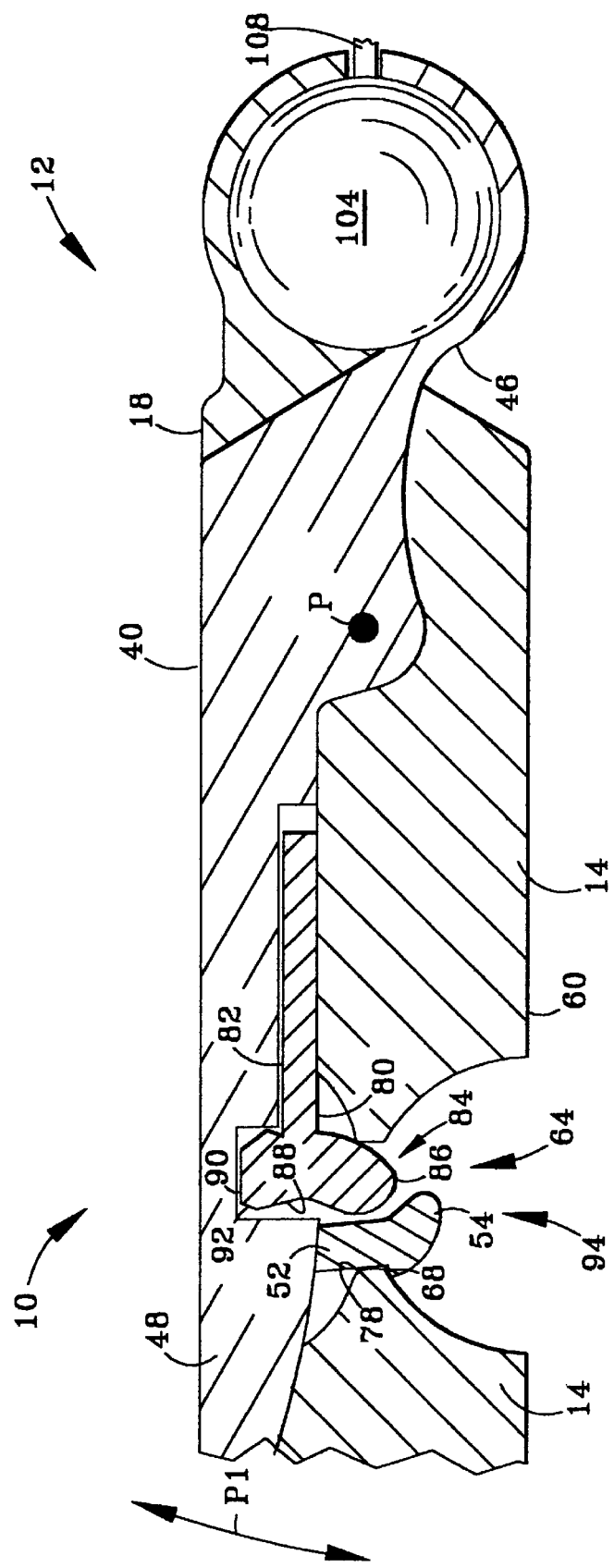
FIG. 12 is similar to FIG. 11, except that the lever arm is in the closed position.

With reference now to FIGS. 11 and 12, the operation of the present invention wherein a latch-receiving member 80 is used is now described. Much of the above discussion pertaining to the embodiment using a lever spring applies to the embodiment using latch-receiving member 80 by analogy.

With reference to FIG. 11 (and also FIG. 4), assuming lever arm 40 is in open position P3, lever arm 40 is depressed toward instrument body 14, thereby bringing concave surfaces 26 and 36 closer to ball-end 104. As lever arm 40 approaches instrument body 14, concave surfaces 26 and 36 begin to engage ball-end 104. Simultaneously therewith, bulbous end 54 of latch 50 contacts top edge 90 and beveled edge 92, causing stem 52 to flex away from member 80. End 54 then passes over top edge 90 and is captured within curved section 88. This position of lever arm 40 is actually a position P3' between intermediate position P2 and open position P3. In position P3', jaws 22 and 32 are sufficiently separated to allow for tool 100 to be removed and replaced, while holding lever arm 40 in position so as to be reachable with a finger. A corresponding position P3' is also possible with the embodiment of the present invention which uses lever spring 74, by adjusting the position and shape of the spring accordingly.

With continuing reference to FIGS. 11 and 12, depressing lever arm 40 toward instrument body 14 causes end 54 to contact rounded section 86, again causing stem 52 to flex away from member 80. End 54 then rounds curved section 86 and engages member 80, with the portion of end 54 closest to lever arm 40 in contact with rounded section 86 at the portion farthest from top edge 90. This puts arm lever in intermediate position P2. At this point, tip 108 can be precisely adjusted to the desired orientation relative to instrument body 14 without risk of tool-end 104 leaving jaws 22 and 32.

As lever arm 40 is brought flush with surface 16 and into closed (i.e., latched) position P1, latch end 54 passes through aperture 64, whereupon stem 52 flexes back into its original shape, thereby causing lip 56 to abruptly overlap (i.e., "snap-latch") with rim 68. Simultaneously therewith, concave surfaces 26 and 36 tightly engage ball-end 104 so as to prevent tool 100 from moving relative to instrument body 14. At this point instrument 10 is ready to be used to perform a dental procedure.

With continuing reference to FIG. 11 and 12, when lip 56 of latch end 54 is disengaged from rim 68 to loosen or release ball-end 104 from jaws 22 and 32, end 54 proceeds through aperture 68. End 54 then engages member 80 such that the portion of end 54 closest to lever arm 40 engages rounded section 86 at the portion farthest from top edge 90 (position P2), as described above. After tip 108 is adjusted to have a desired orientation, lever arm 40 may again depressed and snap-latched into closed position P1, thereby driving jaws 22 and 32 together so that ball-end 104 is tightly engaged by concave surfaces 26 and 36, as described above.

The dental instrument of the present invention has many advantages over prior art dental instruments. A first advantage is that tool 100 can be rapidly replaced with another tool, or the orientation of tip 108 of tool 100 can be rapidly adjusted by snap-latching and snap-releasing lever arm 40. This allows dental procedures to be performed more quickly. Moreover, the latching means allows tool 100 to be held in place with sufficient strength to prevent the tool from moving within jaws 22 and 32 and relative to instrument body 14 while performing dental procedures.

A second advantage is that instrument of the present invention is designed so as to be readily cleansable. For example, concave surfaces 26 and 36 and aperture 64 can be cleaned with brushes. Moreover, the instrument can be readily cleaned when in the open position P3. The present instrument has a configuration similar to forceps, needle holders and the like, and so can be sterilized by scrubbing, ultrasonic cleansing, or autoclaving.

A third advantage is that the mechanisms for latching lever arm 40 and for clasping tool 100 are relatively simple. This not only makes it easy to clean and sterilize the instrument, as described above, but also makes the instrument affordable and easy to use.

Referring to FIG. 10, a fourth advantage is that the ability to quickly adjust and replace tool 100 can be achieved at both ends of instrument 200. This is advantageous when a given dental procedure involves the use of different tools in repeatedly alternating order.

The preferred material for the elements comprising instrument 10 is stainless steel, though other materials, such as plastic, may be used as well.

While the present invention has been described in connection with preferred embodiments, it will be understood that it is not limited to those embodiments. In fact, it will be apparent that the present invention has applications other than that for a dental instrument, and will find utility in applications requiring snap-latching/snap-releasing and adjustment of a ball-end type apparatus requiring a high clasping strength. Accordingly, the present invention is intended to cover all alternatives, modifications and equivalents as may be included within the spirit and scope of the invention as defined in the appended claims.

What is claimed is:

1. An instrument comprising:
   a) an instrument body having a first end;
   b) a first jaw attached to said first end, said first jaw having a first concave surface;
   c) a second jaw having a second concave surface;
   d) a lever arm having first and second ends, said first end being attached to said second jaw, wherein said lever arm is pivotally attached to said instrument body adjacent said first end so as to be pivotable from a first position;
   e) an aperture located in one of said body and said lever arm, said aperture having a rim;
   f) a latch attached to the other of said lever arm and said instrument body, said latch including an end having a lip, wherein said end is sized to fit through said aperture such that said lip engages said rim of said aperture when said lever arm is in said first position; and
   g) a tool having a spherical ball-end that is sized to be tightly engaged by said first and second concave surfaces when said lever arm is in said first position so as to prevent said tool from moving relative to said instrument body.

2. An instrument according to claim 1, further including a first depression in said surface surrounding said aperture, said first depression designed to receive a person's finger.

3. An instrument according to claim 1, further including a lever spring attached to said instrument body adjacent said latch such that when said lip is disengaged from said rim, said latch is releasably held by said lever spring in an intermediate position.

4. An instrument according to claim 1, further including a latch-receiving member attached to said instrument body adjacent said latch such that when said lip is disengaged from said rim, said latch is releasably held by said receiving member in an intermediate position.

5. An instrument according to claim 1, further including a side having a depression formed therein, where a portion of said lever arm extends into said depression so as to allow a person's finger to engage said lever arm.

6. An instrument according to claim 1, wherein:
   a) said first and second concave surfaces each have an outer edge with teeth formed therein; and
   b) said tool an includes an instrument tip and a neck located between said ball-end and said instrument tip, wherein said neck includes teeth formed therein designed so as to mesh with said outer edge teeth when said lever arm is in said first position.

7. An instrument according to claim 1, wherein said ball-end comprises a compressible material.

8. An instrument according to claim 1, wherein said ball-end comprises an incompressible material.

9. An instrument according to claim 1, wherein said latch is attached to said lever arm and said aperture is located in said instrument body.

10. An instrument according to claim 1, further including a compressible liner on said first and second concave surfaces to facilitate gripping said spherical ball-end.

11. An instrument comprising:
   a) an instrument body having a first end and a second end;
   b) a first jaw attached to said first end, said first jaw having a first concave surface;
   c) a second jaw having a second concave surface;
   d) a lever arm having first and second ends, said first end being attached to said second jaw, wherein said lever arm is pivotally attached to said instrument body adjacent said first end so as to be pivotable from a first position;
   e) a latch attached to one of said lever arm and said instrument body that releasably grips the other of said lever arm and said instrument body so as to retain said lever arm in said first position;
   f) a tool having a spherical ball-end that is sized to be tightly engaged by said first and second concave surfaces when said lever arm is in said first position so as to prevent said tool from moving relative to said instrument body;
   g) a third jaw attached to said second end, said third jaw having a third concave surface;
   h) a fourth jaw having a fourth concave surface;
   i) a second lever arm having first and second ends, said first end being attached to said third jaw, wherein said lever arm is pivotally attached to said instrument body adjacent said second end so as to be pivotable from a first position;
   j) a second latch attached to one of said second lever arm and said instrument body that releasable grips the other of said second lever arm and said instrument body so as to retain said second lever arm is said first position; and
   k) a second tool having a spherical ball-end that is sized to be tightly engaged by said third and fourth concave surfaces when said second lever arm is in said first position so as to prevent said second tool from moving relative to said instrument body.

12. An instrument for clasping a tool having a ball-end and a neck, comprising:
   a) an elongate body having first and second ends, a longitudinal axis and an outer surface extending at least a portion of the length of said elongate body, said body including a recess in said outer surface, said recess being parallel to said longitudinal axis;
   b) a first jaw having a concave surface, said first jaw fixedly attached to said elongate body at said first end of said elongate body;
   c) a lever arm having first and second ends and a pivot point located therebetween, said lever arm being pivotally attached at said pivot point to said elongate body adjacent said first end of said elongate body so as to be pivotable from a first position, said recess of said elongate body receiving at least a portion of said second end of said lever arm when said lever arm is in said first position;
   d) a second jaw having a concave surface, said second jaw fixedly attached to said first end of said lever arm such that said concave surface of said second jaw faces said concave surface of said first jaw; and
   e) a latch attached to one of said lever arm and said elongate body, said latch for releasably securing said lever arm to said body when said lever arm is in said first position.

13. An instrument according to claim 12, wherein first teeth are provided on the neck of the tool, further wherein at least one of said first and second jaws has an outer edge with second teeth formed therein, said first and second teeth designed to mesh with one another when said lever arm is in said first position.

14. An instrument according to claim 12, wherein said outer surface of said body has a depression formed therein so as to allow a person's finger to engage said lever arm.

15. An instrument according to claim 12, wherein said latch is attached to said lever arm and extends into an aperture within said elongate body when said lever arm is in said first position.

16. An instrument according to claim 12, wherein said lever arm has an outer surface, said outer surface of said lever arm and said outer surface of said elongate body being substantially flush with one another when said lever arm is in said first position.

17. An instrument according to claim 16, wherein said outer surface of said lever arm and said outer surface of said elongate body form a cylindrical shape when said lever arm is in said first position.

18. A method of adjusting a dental instrument having a tool with a ball end and a tip, comprising the steps of:
   a) providing a dental instrument according to claim 17;
   b) adjusting said first and second jaws to an open position and placing the ball-end within said first and second jaws;
   c) adjusting said first and second jaws to said first intermediate position and adjusting the tip to a first desired orientation; and d) moving said lever arm to said closed position such that said first part of said first detent engages said second part of said first detent.

19. A method of adjusting a dental instrument according to claim 18, further comprising the steps, after said step d), of:

e) performing a dental procedure;
   f) snap-releasing said jaws to said first intermediate position and adjusting the tip to a desired orientation; and
   g) repeating said step d).

20. An instrument for clasping a tool having a ball-end, comprising:

a) a body having a first end;
   b) a first jaw rigidly attached to said first end of said body, said first jaw having a first concave surface;
   c) a second jaw having a second concave surface;
   d) a lever arm having first and second ends and a pivot point located therebetween, said second jaw being rigidly attached to said first end of said lever arm, said lever arm being pivotally attached to said body such that said lever arm is pivotable with respect to said body about said pivot point between a closed position wherein said first and second concave surfaces clampingly engage the ball end of the tool and a full-open position wherein said second concave surface is spaced from said first concave surface; and
   e) a teethless detent mechanism for holding said lever arm in fixed relationship to said body when said lever arm is in said closed position and when said lever arm is in a first intermediate position between said closed position and said full-open position, said teethless detent mechanism comprising:
      i) a first detent having a first part attached to one of said lever arm and said body and a second part located on the other of said lever arm and said body, said first part engaging said second part when said lever arm is in its closed position; and
      ii) a second detent having a first part attached to one of said lever arm and said body and a second part located on the other of said lever arm and said body, said first part engaging said second part when said lever arm is in its closed position.

21. An instrument according to claim 20, wherein said first part of said first detent comprises a latch having a lip, said second part of said first detent comprising a stop, said lip engaging said stop when said lever arm is in said closed position.

22. An instrument according to claim 20, wherein said first part of said second detent comprises a resilient latch having a first contact surface, said second part of said second detent comprising a second contact surface, said first contact surface frictionally contacting said second contact surface so as to hold said lever arm in said first intermediate position.

23. An instrument according to claim 20, wherein said first part of said second detent comprises a latch having a first contact surface, said second part of said second detent comprising a resilient member having a second contact surface, said first contact surface interferingly contacting said second contact surface so as to hold said lever arm in said first intermediate position.

24. An instrument according to claim 20, wherein said teethless detent mechanism further comprises a third detent, said third detent adapted to hold said lever arm in fixed relationship to said body in a second intermediate position between said first intermediate position and said full-open position, said third detent comprising a first part attached to one of said lever arm and said body and a second part located on the other of said lever arm and said body.

25. An instrument according to claim 20, wherein said first part of said third detent comprises a latch having a first contact surface and said second part of said third detent comprises a resilient member having a second contact surface, said first contact surface frictionally engaging said second contact surface so as to hold said lever arm in said second intermediate position.

* * * * *

UNITED STATES PATENT AND TRADEMARK OFFICE
CERTIFICATE OF CORRECTION

PATENT NO. : 6,193,514 B1  
DATED : February 27, 2001  
INVENTOR(S) : Terrence L. Horan Page 1 of 1

It is certified that error appears in the above-identified patent and that said Letters Patent is hereby corrected as shown below:

Column 10,  
Line 61, delete "17" and substitute therefor -- 20 --;

Column 12,  
Line 32, delete "20" and substitute therefor -- 24 --.

Signed and Sealed this

Thirteenth Day of November, 2001

Attest:

*Nicholas P. Godici*

*Attesting Officer*

NICHOLAS P. GODICI  
*Acting Director of the United States Patent and Trademark Office*